United States Patent [19]

Simmons

[11] 4,162,625
[45] Jul. 31, 1979

[54] METHOD AND APPARATUS FOR FORMING DENTAL COPINGS

[76] Inventor: David E. Simmons, 3600 Prytania St., New Orleans, La. 70115

[21] Appl. No.: 871,810

[22] Filed: Jan. 24, 1978

[51] Int. Cl.$^2$ .............................................. B21D 22/12
[52] U.S. Cl. ........................................ 72/54; 72/465; 72/DIG. 14; 32/42
[58] Field of Search .............. 72/57, 54, 465, DIG. 14; 29/160.6; 32/12, 42

[56] References Cited

U.S. PATENT DOCUMENTS

| 906,911 | 12/1908 | McCullough | 32/12 |
| 1,012,401 | 12/1911 | McCullough | 72/57 |
| 2,422,883 | 6/1947 | Bruderlin | 72/DIG. 14 |

FOREIGN PATENT DOCUMENTS 586168  3/1947  United Kingdom .......................... 72/57

Primary Examiner—Lowell A. Larson
Attorney, Agent, or Firm—Keaty and Garvey

[57] ABSTRACT

A method and apparatus for forming dental matrices and copings is disclosed. The apparatus provides a first and a second compression member, each of which is provided with a pliable surface thereon. One of the compression members has a point for the attachment of a conventionally formed tooth die thereto, upon which a sheet of conventional coping material can be placed. The compression members are attachable to a jacking apparatus which imparts relative motion to the two compression members urging them together and compressing the tooth die therebetween the sheet of coping material conforming to the shape of the tooth die itself. In the method of the present invention, the first and second compression members are placed a distance apart, and the tooth die attached to one of the compression members at its pliable surface. The sheet of coping material is then loosely attached to the tooth die, after which the first and second compression members are urged together and compressed so as to cause the pliable surface of each compression member to substantially conform to and abut the tooth die, putting substantially uniform pressure thereon. The sheet of coping material then substantially conforms to the tooth die forming the desired coping.

22 Claims, 12 Drawing Figures

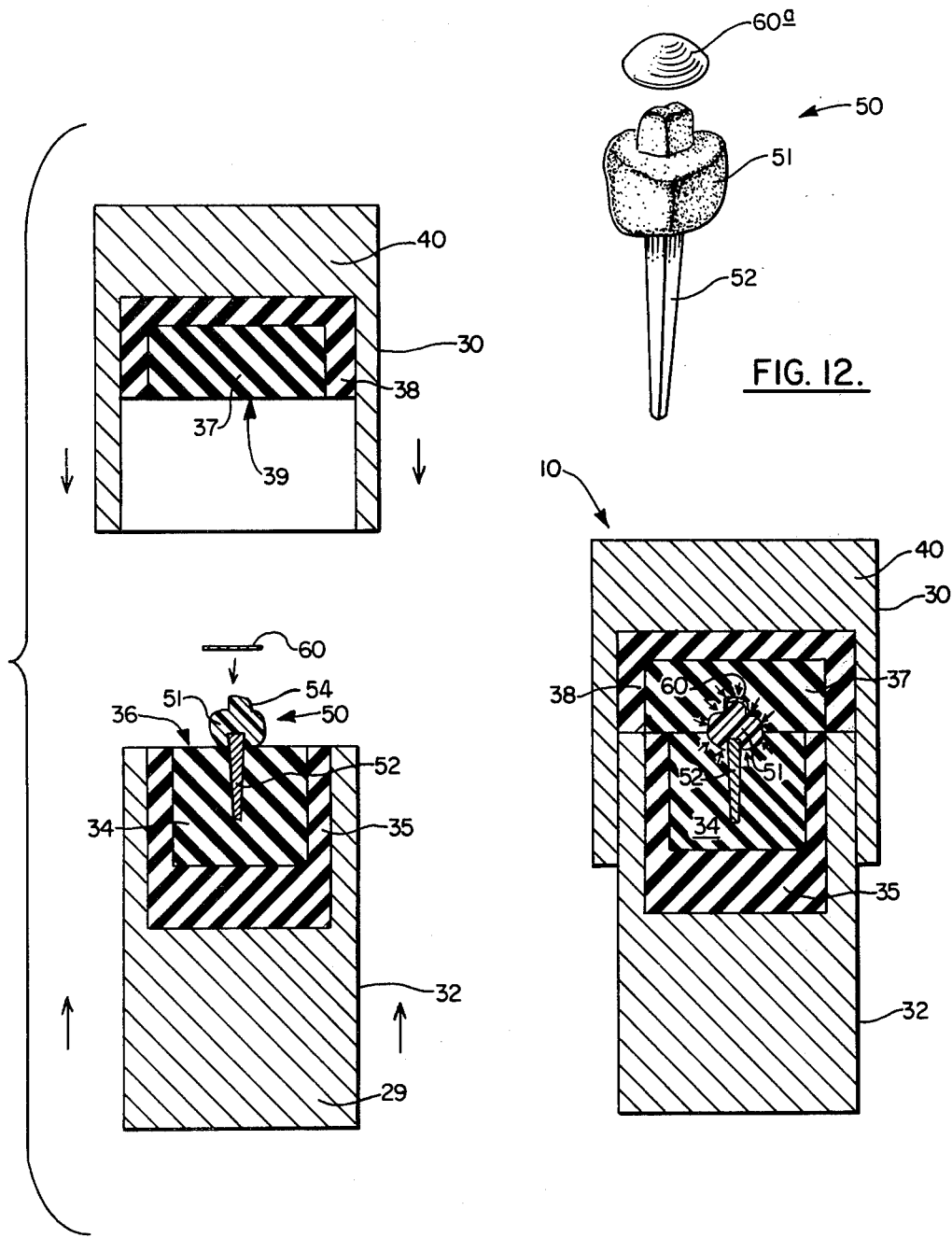

METHOD AND APPARATUS FOR FORMING DENTAL COPINGS

BACKGROUND OF THE INVENTION

1. Field of the Invention

The present invention relates to dental equipment and more particularly relates to a method and apparatus for forming metal copings and matrices.

2. General Background and Prior Art

In forming crowns, a new popular technique is the McClean-Sced technique. In this technique, aluminous porcelain is fused to thin platinum foil copings. With the McClean-Sced process, the copings can be of a substantially reduced thickness on the order of one to two thousandths (0.025mm or 0.05mm) of an inch. Thus, the cost of metal for the individual metal-ceramic crowns is reduced. The McClean-Sced process relies on the electro-deposition of a very thin coating of pure tin on the surface of the foil coping. Subsequent oxidation of this tin-coated platinum foil causes the tin to alloy and oxidize on the platinum surface. The continuous film of tin oxide provides a perfect medium for porcelain bonding. The electro-deposition process allows automatic timing of the coating process and is also used to degrease the surface of the matrix before applying the tin. The accuracy of the timing apparatus ensures that only a very thin coat of tin is applied and this should not be greater than 0.5 to 1 mincons thick.

The tooth preparation should conform to the standard aluminous porcelain jacket crown preparation.

Before the present invention, the foil has been applied to the die and conformed thereto by a procedure using a "tinner's joint."

The use of the "tinner's joint" provides an undesireable fold in the foil sheet which thereafter causes problems when the porcelain is to be added to the coping in the standard jacket crown process.

In the prior art method of forming the matrices or copings, which method uses the "tinner's joint," the foil is made to conform to the shape of the tooth die by means of manual burnishing. This procedure is time consuming and also undesireable because of the aforementioned problem of the "fold" produced by the "tinner's joint" which thereafter leaves a thickened area to which the porcelain is not as well adhered.

GENERAL DISCUSSION OF THE PRESENT INVENTION

The present invention solves the problems and shortcomings of the prior art by providing a method and apparatus for forming dental matrices or copings which removes the need for forming a "tinner's joint," and forms the coping with no folds thereon and without the need for time consuming hand burnishing.

In the apparatus of the present invention, there is provided a pair of compression members, each compression member providing thereon a pliable surface which surface normally contacts the tooth die during the process in which the coping is formed. A standard tooth die is formed by means known in the art and then attached first to one of the compression members at its pliable surface. Thereafter, a thin sheet of coping material is roughly placed over the tooth die. A second compression member is then coverably connected to the first compression member and the two compression members urged together by a jack which causes the two respective pliable surfaces to abutt and conform to the area around the tooth die and attached sheet of coping material. In this process, the tooth die is surrounded by a pliable material which "gives" so as to substantially conform the pliable surfaces of the compression members to the configuration of the tooth die, creating a substantially uniform pressure which urges the sheet of coping material into substantial conformity with the surface of the tooth die itself as is desireable.

BRIEF DESCRIPTION OF THE DRAWINGS

For a further understanding of the nature and objects of the present invention, reference should be had to the following detailed description, taken in conjunction with the accompanying drawings, in which like parts are given like reference numerals and wherein:

FIG. 10 is a front, sectional view of the first and second compression member portions of the preferred embodiment of the present invention illustrating the attachment of a conventional tooth die thereto; and FIG. 11 is a sectional, elevational view of the preferred embodiment of the apparatus of the present invention illustrating the first and second compression member in their operative state urging a foil coping onto the tooth die.

FIG. 12 is a perspective view of a shaped coping and tooth die.

DETAILED DESCRIPTION OF THE PREFERRED EMBODIMENT

Structure

Figure 4:
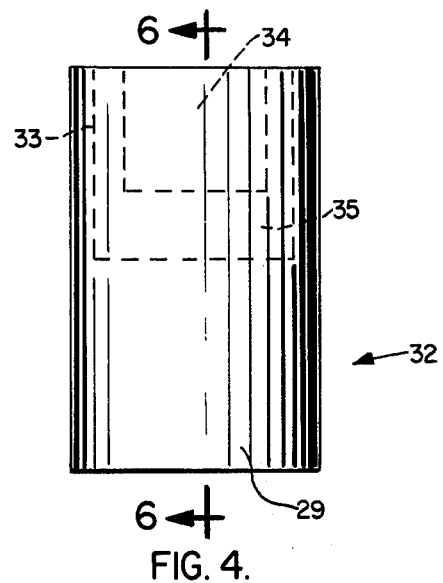
FIG. 4 is a front view of the second compression member portion of the preferred embodiment of the apparatus of the present invention.
Figure 9:
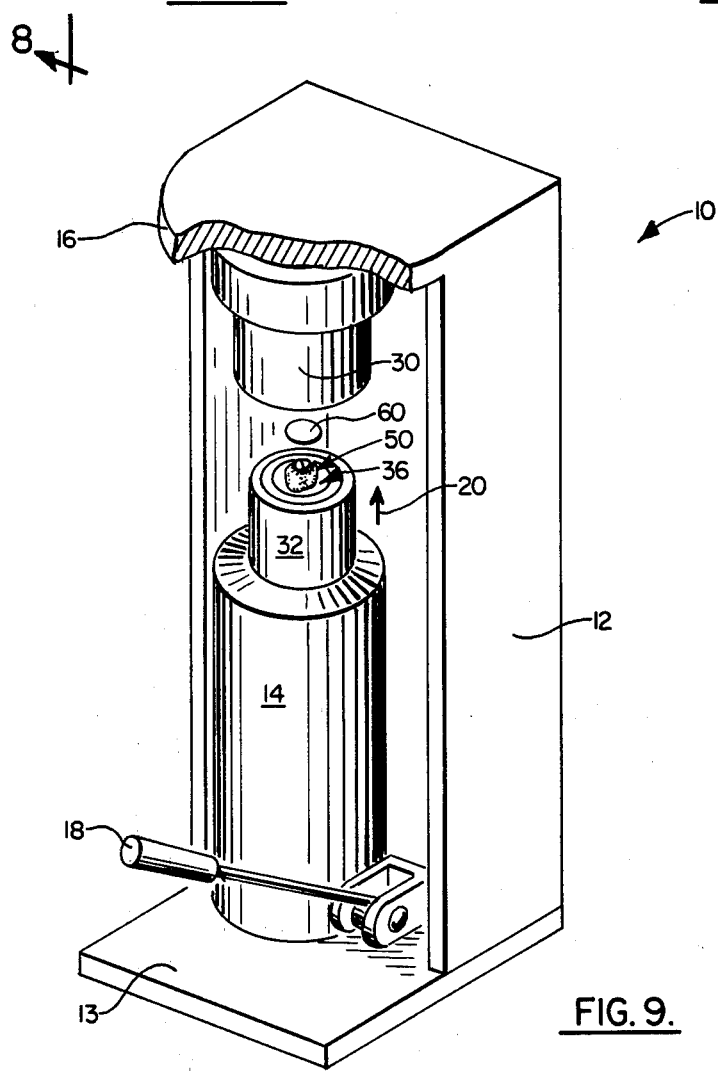
FIG. 9 is a perspective view of the preferred embodiment of the apparatus of the present invention.

FIG. 9 best illustrates the preferred embodiment of the apparatus of the present invention designated generally by the numeral 10 in FIG. 9. The apparatus 10 is comprised generally of a frame 12 having a base portion 13 with a telescoping pedestal 14 attached thereto. Pedestal 14 can be operated as any conventional jack by means of lever 18 as is known in the art. The upper portion of pedestal 14 is provided with a lower compression member 32 (see FIGS. 2 and 4) having a pliable upper surface 36 thereon. A conventional tooth die 50 can be placed thereon after its formation by means known in the art.

An upper compression member 30 (see FIGS. 1-2) also having a pliable surface thereon (not shown in FIG. 9) is provided at the upper portion of frame 12 and attached to roof member 16. It can be seen from the above, that a compressive effect (as will be more fully discussed hereinafter) can be achieved upon tooth die 50 when compression members 30, 32 are urged together by operation of lever 18, urging lower compression member 32 upwardly in the direction shown by the arrow 20 in FIG. 9.

Figure 1:
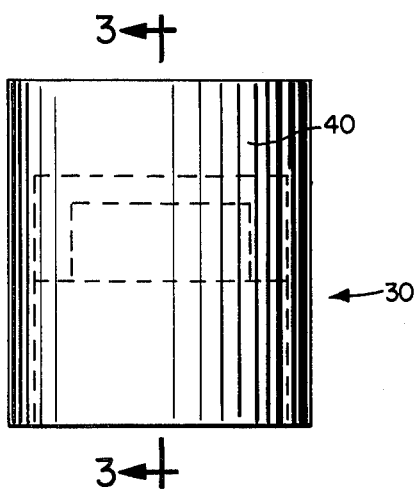
FIG. 1 is a front view of the first compression member portion of the preferred embodiment of the apparatus of the present invention.
Figure 2:
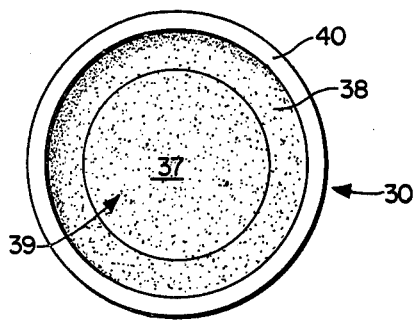
FIG. 2 is a bottom view of the first compression member portion of the preferred embodiment of the apparatus of the present invention illustrating the pliable surface thereon.
Figure 5:
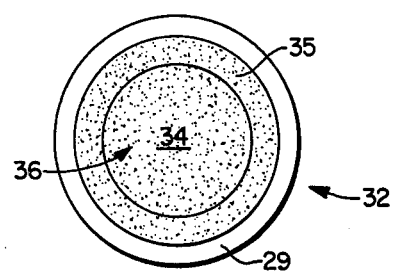
FIG. 5 is a top view of the second compression member portion of the preferred embodiment of the apparatus of the present invention illustrating the pliable surface thereon.
Figure 3:
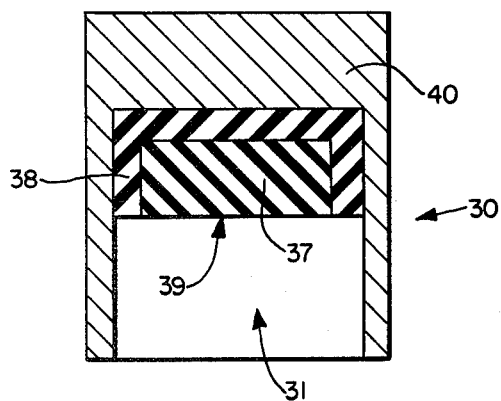
FIG. 3 is a sectional view taken along lines 3—3 of FIG. 1.
Figure 6:
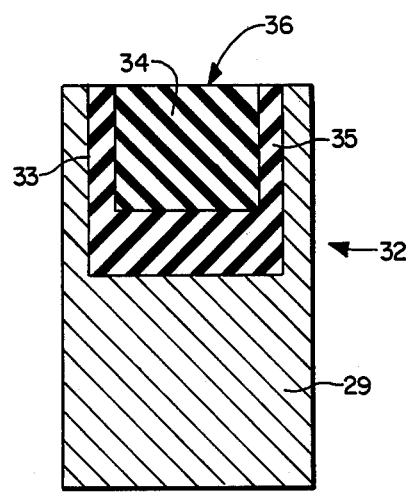
FIG. 6 is a sectional view taken along lines 6—6 of FIG. 4.

FIGS. 1-6 best illustrate in detail the construction of the upper compression member 30 and lower compression member 32. In FIGS. 1-3, there can be seen upper compression member 30 which is comprised of an outer substantially rigid housing 40 having an inner formed recess 31 which is filled with a first semi-hardened liner 38 and a second pliable insert 37. The combination of liner 38 and pliable insert 37 provides a pliable surface 39 as is shown best in FIGS. 2 and 3.

In a like manner, lower compression member 32 is provided with an inner recess 33 which is lined with liner 35 of a preferably harder material, and insert 34 of a softer material such as gum rubber or the like. Thus, a pliable surface 36 is also provided with compression member 32 as was described above for compression member 30.

Housings 29, 40 can be of any substantially rigid structural material such as steel, iron, or like metal. A suitable hard plastic material could likewise be used.

The innermost liner 38 of upper compression member 30 can be manufactured of a suitable semi-hard material such as specified by the American Dental Association as "hard rubber" — a Type 1 polysulfide rubber base material being suitable as a material for liner 38. Insert 37 can be of any pliable soft material such as a soft rubber. A suitable material would be Type 1, Class 2 light body polysulfide base rubber according to American Dental Association specifications.

The liner 35 portion of lower compression member 32 can be of any suitable plastic material such as polypropylene, polyvinyl chloride and the like. Insert 34 would preferably be of a pliable rubber such as gum rubber, latex or the like.

Operation

Figure 7:
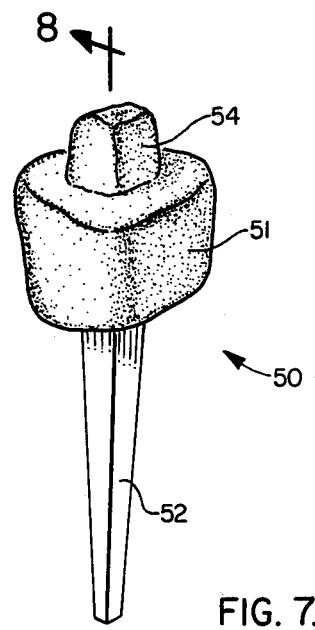
FIG. 7 is a perspective view of a conventional tooth die as is used in the art.
Figure 8:
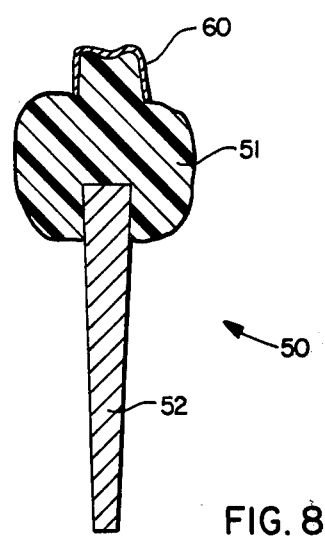
FIG. 8 is a sectional view taken along lines 8—8 of FIG. 7.

FIGS. 7, 8, 9 and 10 illustrate more particularly the method of operation of the apparatus of the present invention. In FIG. 7, there can be seen a tooth die 50 formed by conventional methods, which is comprised of a dowel pin 52 having a silver plated dental stone or epoxy upper portion 51 attached thereto, which upper portion provides a die surface 54 which conforms exactly to the tooth of the individual to which a crown will be applied. Coping 60 will be applied by the method and apparatus of the present invention to die 50 and will conform substantially to die surface 54. Coping 60 is shown in FIG. 8 in its conforming position about tooth die 50 at die surface 54. A suitable material for use as coping 60 would be dead soft platinum foil on the order of, for example 0.001 inches to 0.002 inches in thickness. Such a foil is manufactured by Englehard Materials Chemicals Corporation, Baker Dental Division. Foil copings 60 could be pre-formed made to a size and shape generally conforming to prepared teeth, with the method and apparatus of the present invention providing the compressive force necessary to conform the coping substantially to the tooth (or die thereof) itself. Such a "shaped coping" is shown in FIG. 12.

Shaped coping 60A could be manufactured in a variety of shapes depending on the particular tooth member with which it would be used. Such a shaped coping would be especially useful for use with more elongated teeth such as incisors.

In FIGS. 10 and 11, there can be seen upper and lower compression members 30, 32. In FIG. 10, an exploded view is provided showing tooth die 50 mounted upon pliable surface 36 of lower compresssion member 32. A sheet of coping material 60 is shown in a position above die surface 54 and its attachment thereto. Upper compression member 30 is suspended above lower compression member 32 prior to its cooperative connection thereto.

In FIG. 11. there can be seen the completed operation of the apparatus 10 of the present invention at which point the lower compression member 32 and upper compression member 30 have been urged together to compress die 50 therebetween. Note that the pliable surfaces 39, 36 respectively of upper and lower compression member 30, 32 have deformed and conformed to the outline of die 50. This is of importance in the operation of the present invention because each of the pliable surfaces 36, 39 "gives" so as to prevent tearing of the coping material 60 when it is forced against die 50 for comforming thereto. When the pliable surfaces give, as is illustrated in FIG. 11, a substantially equal pressure is applied to the surface of die 50 (see Arrows, FIG. 11).

The pliable nature of surfaces 36, 39 causes substantially uniform pressure to be applied to coping 60 and tooth die 50, thereby allowing the coping to be attached to and conformed substantially to the die 50 without tearing, as occurs at times with hand burnishing, where a rigid base is usually provided for attachment of the die 50.

Because many varying and different embodiments may be made within the scope of the inventive concept herein taught, and because many modifications may be made in the embodiments herein detailed in accordance with the descriptive requirements of the law, it is to be understood that the details herein are to be interpreted as illustrative and not in a limiting sense.

I claim:

1. An apparatus for forming dental copings comprising:
   a. a first compression member providing a first pliable compression surface;
   b. a tooth die attachable to the surface of said first compression member at said first pliable surface;
   c. a second compression member in cooperative relationship to said first compression member said second compression member providing a second pliable compression surface;
   d. a sheet of coping material sized to coverably fit over said tooth die; and
   e. compression means for urging said first compression and said second compression member together, said sheet of coping material being deformed to substantially conform to the shape of said tooth die when said first compression member and said second compression member are urged together by said compression means.

2. The apparatus of claim 1 wheren said sheet of coping material is generally sized to conform to the shape of said tooth die.

3. The apparatus of claim 1, wherein said first compression member provides a pliable surface thereon and said tooth die is attachable to said first compression member at said pliable surface.

4. The apparatus of claim 3, wherein said second compression member provides a pliable surface thereon and said pliable surface on said second compression member at least partially abuts said tooth die when said first compression member and said second compression member are urged together by said compression means.

5. The apparatus of claim 1 wherein said first compression member is comprised of:
   a. an outer, rigid body; and
   b. an inner, pliable insert having a pliable surface.

6. The apparatus of claim 5, wherein said second compression member is comprised of an outer rigid body and an inner pliable insert providing a pliable surface.

7. The apparatus for forming dental copings of claim 1 wherein said sheet of coping material has a thickness of 0.0002 inches or less.

8. The apparatus for forming dental copings of claim 1 wherein at least one of said pliable surfaces is rubber.

9. The apparatus for forming dental copings of claim wherein at least one of said pliable surfaces is gum rubber.

10. The apparatus for forming dental copings of claim 1 wherein said compression means is a jack.

11. An apparatus for forming dental copings comprising:
    a. a tooth die
    b. a sheet of coping material sized to coverably fit over said tooth die; and
    c. uniform compression means providing a pliable surface substantially surrounding said tooth die and said sheet of coping material for urging said sheet of coping material into conforming contact with said tooth die, said uniform compression means applying substantially equal pressure to the surface of said sheet of coping material to urge it into conformity with said tooth die.

12. The apparatus of claim 11, wherein a portion of said tooth die provides a contoured surface, which surface conforms to the shape of a human tooth to which a dental coping will be attached.

13. The apparatus of claim 11 wherein said compression means is comprised of a first compression member and a second compression member, and a jack means for urging said first and second compression members together, and one of said compression members provides a point of attachment for said tooth die. 14.

14. The apparatus for forming dental copings of claim 11 wherein said sheet of coping material has a thickness of between 0.001 inches to 0.002 inches.

15. The apparatus for forming dental copings of claim 11 wherein said uniform compression means comprises a pair of pliable compression surfaces and jack means cooperatively connected to said pair of pliable compression surfaces for urging said pair of surfaces together.

16. A method for forming dental copings comprising the steps of:
    a. providing a tooth die;
    b. covering a portion of the tooth die with a sheet of coping material; and
    c. applying substantially uniform pressure through a surrounding pliable surface to the sheet of coping material and the tooth die, whereby the sheet of coping material responsive to uniform pressure substantially forms to the shape of the tooth die.

17. The method for forming dental copings of claim 16 wherein in step C, a jack is utilized to apply the substantially uniform pressure through a pair of pliable surfaces urged together by the jack.

18. The method for forming dental copings of claim 17 wherein each pliable surface deforms and conforms to the outline of the tooth die compressed therebetween.

19. The method of forming dental copings of claim 16 wherein in step C the uniform pressure is applied to the sheet of coping material and the tooth die by a pair of rubber like compression surfaces which urge the sheet of coping material into conformity with the tooth die while compressing the tooth die and sheet of coping material therebetween.

20. The method of claim 16, wherein there is provided the further steps between steps a and b of:
    providing a first pliable rubber compression member;
    placing the tooth die on the surface of said pliable rubber compression member;
    providing a second pliable rubber compression member; and
    in step c, the uniform pressure is applied to the sheet of coping material and the tooth die by urging the first and second compression members together, with the tooth die therebetween.

21. The method for forming dental copings of claim 20 wherein in step C the uniform pressure is applied to the sheet of coping material and the tooth die by urging the first and second compression members together with the tooth die therebetween by means of jacking.

22. An apparatus for forming dental copings comprising:
    a. a first compression member, said compression member comprising an outer rigid housing having an inner formed recess holding a first pliable rubber insert;
    b. a second lower compression member comprising an outer rigid housing having an inner formed recess holding a second pliable rubber insert;
    c. Jack means cooperatively connecting said first compression and said second compression member for urging said first compression and said lower compression member together in a direction which forces said first pliable insert and said second pliable inserts together;
    d. means on at least one of said compression members for providing a point of attachment for a dental die, said first and said second compression members applying through said first and second pliable rubber inserts substantially uniform pressure to the outer surface of said die, substantially conforming a portion of said pliable inserts to the surface of the dental die and an affixed sheet of coping material to be shaped.

* * * * *